(12) United States Patent
Holland

(10) Patent No.: US 7,570,893 B2
(45) Date of Patent: Aug. 4, 2009

(54) METHODS OF MONITORING A MARKING LIQUID, APPARATUSES FOR MONITORING A MARKING LIQUID, AND IMAGE TRANSFER DEVICES

(75) Inventor: William David Holland, Palo Alto, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 306 days.

(21) Appl. No.: 11/444,565

(22) Filed: Jun. 1, 2006

(65) Prior Publication Data

US 2007/0280712 A1 Dec. 6, 2007

(51) Int. Cl.
*G03G 15/10* (2006.01)

(52) U.S. Cl. .................. 399/30; 399/237; 73/61.71; 73/597

(58) Field of Classification Search .................. 399/30, 399/237; 430/117.1; 347/19, 119; 340/618; 73/61.71, 1.86, 32 A, 54.41, 61.75, 61.79, 73/64.53, 597, 599, 602
See application file for complete search history.

(56) References Cited

U.S. PATENT DOCUMENTS

| | | | |
|---|---|---|---|
| 3,283,644 A | 11/1966 | Saltzman | |
| 3,518,003 A | 6/1970 | Meyn | |
| 3,724,957 A | 4/1973 | Tamate et al. | |
| 3,954,119 A | 5/1976 | Kunioka et al. | |
| 4,166,394 A | 9/1979 | Figura | |
| 4,166,702 A | 9/1979 | Okamoto et al. | |
| 4,171,916 A | 10/1979 | Simms et al. | |
| 4,215,575 A * | 8/1980 | Akita et al. | 374/119 |
| 4,478,072 A | 10/1984 | Brown | |
| 4,579,253 A | 4/1986 | Shenier | |
| 4,630,482 A | 12/1986 | Traina | |
| 4,660,152 A | 4/1987 | Downing et al. | |
| 4,726,235 A | 2/1988 | Leffert et al. | |
| 4,934,177 A | 6/1990 | Cuthbertson et al. | |
| 5,121,629 A | 6/1992 | Alba | |
| 5,226,317 A | 7/1993 | Irie et al. | |
| 5,473,934 A | 12/1995 | Cobb | |
| 5,569,844 A * | 10/1996 | Sowerby | 73/61.75 |
| 5,570,193 A | 10/1996 | Landa et al. | |
| 5,737,666 A * | 4/1998 | Lior et al. | 399/57 |
| 5,793,490 A | 8/1998 | Forgacs et al. | |
| 5,831,150 A * | 11/1998 | Sowerby et al. | 73/61.75 |
| 7,010,979 B2 * | 3/2006 | Scott | 73/596 |
| 2004/0093948 A1 | 5/2004 | Kelner et al. | |

FOREIGN PATENT DOCUMENTS

| | | |
|---|---|---|
| EP | 0233047 | 8/1987 |
| JP | 59083177 A * | 5/1984 |
| JP | 2001142306 | 5/2001 |
| WO | WO 2004020112 | 3/2004 |

\* cited by examiner

*Primary Examiner*—David M Gray
*Assistant Examiner*—G. M. Hyder

(57) ABSTRACT

A method and apparatus for monitoring marking liquid including a carrier liquid having solid particles therein. A transmitter emits an ultrasonic signal into the marking liquid. The ultrasonic signal is received by a receiver and processed by a controller to determine at least one of the temperature of the marking liquid and the concentration of solid particles in the marking liquid.

21 Claims, 6 Drawing Sheets

US 7,570,893 B2

METHODS OF MONITORING A MARKING LIQUID, APPARATUSES FOR MONITORING A MARKING LIQUID, AND IMAGE TRANSFER DEVICES

BACKGROUND OF THE INVENTION

The present invention generally relates to image transfer technology and, more particularly, to an apparatus and method for monitoring a marking liquid in an image transfer device, and an image transfer device utilizing the apparatus and method.

As used herein, the term "image transfer device" generally refers to all types of devices and systems used for creating and/or transferring an image in an imaging process, including laser printers, copiers, facsimiles, and the like. An electrophotographic process is one exemplary imaging process. As used herein, the term "electrophotographic process" includes both dry and liquid electrophotographic (LEP) processes.

In an electrophotographic image transfer device, the surface of a photoconducting material (i.e., a photoreceptor) is charged to a substantially uniform electrostatic potential so as to sensitize the surface. An electrostatic latent image is created on the surface of the charged photoconducting material by selectively exposing areas of the photoreceptor surface to a light image of the original document being reproduced. A difference in electrostatic charge density is created between the areas on the photoreceptor surface exposed and unexposed to light. The electrostatic latent image on the photoreceptor surface is developed into a visible image using electrostatic toners or pigments. The toners are selectively attracted to the photoreceptor surface either exposed or unexposed to light, depending on the relative electrostatic charges of the photoreceptor surface, development electrode, and toner. The photoreceptor surface may be either positively or negatively charged, and the toner system similarly may contain negatively or positively charged particles. An intermediate transfer member is passed close to the photoreceptor surface, which may be in the form of a rotating drum or belt, transferring the toner from the photoreceptor surface onto the intermediate transfer member in the pattern of the image developed on the photoreceptor surface. A sheet of paper or other medium is then passed close to the intermediate transfer member, which may be in the form of a rotating drum or belt, transferring the toner from the intermediate transfer member onto the paper, thereby forming a hard image. In some image transfer devices, no intermediate transfer member is used, and the paper or other medium is passed close to the photoreceptor surface to form a hard image.

In some image transfer devices, the toners or pigments used to develop the electrostatic latent image on the photoreceptor surface are delivered to the photoreceptor surface in a suspension or dispersion with another material that acts as a carrier or vehicle for the toners or pigments. In such systems, there are process and material parameters that need to be stabilized at consistent and well-controlled values to ensure a high image quality. For example, the concentration of toners or pigments in the carrier affects the quality of the hard image produced by the image transfer device, as does the temperature of the carrier and toners or pigments therein. If these parameters go outside of a desired range, the quality of the hard image is adversely impacted. Accordingly, sensors for determining the concentration of particles (e.g., toners or pigments) in the carrier, temperature, and other material or process parameters (e.g., conductivity, fluid level, etc.) may be utilized.

Methods and apparatuses for determining particle concentration, temperature, and other material or process parameters in image transfer devices are known and successfully implemented. However, improved methods and apparatuses for determining particle concentration and temperature are always desirable. Improved methods and apparatuses may reduce complexity, reduce costs, improve accuracy, require less frequent calibration, require less cleaning, be less sensitive to color cross-contamination, or provide a greater range of measurement.

SUMMARY OF THE INVENTION

The invention described herein provides a method and apparatus for monitoring marking liquid. In one embodiment the method comprises: emitting an ultrasonic signal from an emitter into the marking liquid; receiving first and second reflected ultrasonic signals from a first reflector and a second reflector, respectively, in the marking liquid, wherein the emitter, first reflector and second reflector are in known positions relative to each other; and processing the first and second reflected ultrasonic signals to determine at least one of the temperature of the marking liquid and the concentration of solid particles in the marking liquid.

In one embodiment, the apparatus comprises: a transmitter for sending an ultrasonic signal into the marking liquid; a receiver for receiving the ultrasonic signal; and a controller responsive to the received signal, the controller configured to determine ultrasonic attenuation and ultrasonic velocity of the marking liquid, and further configured to determine at least one of the temperature of the marking liquid and the concentration of solid particles in the marking liquid using predetermined relationships between ultrasonic attenuation, ultrasonic velocity, marking liquid temperature and solid particles concentration.

In another embodiment, the apparatus comprises: a transmitter for sending an ultrasonic signal into marking liquid; a first reflector configured to reflect a first portion of the ultrasonic signal; a second reflector configured to reflect a second portion of the ultrasonic signal; a receiver for receiving first and second reflected ultrasonic signals from the first and second reflectors, respectively; and a controller responsive to the first and second reflected ultrasonic signals to determine at least one of the temperature of the marking liquid and the concentration of solid particles in the marking liquid.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
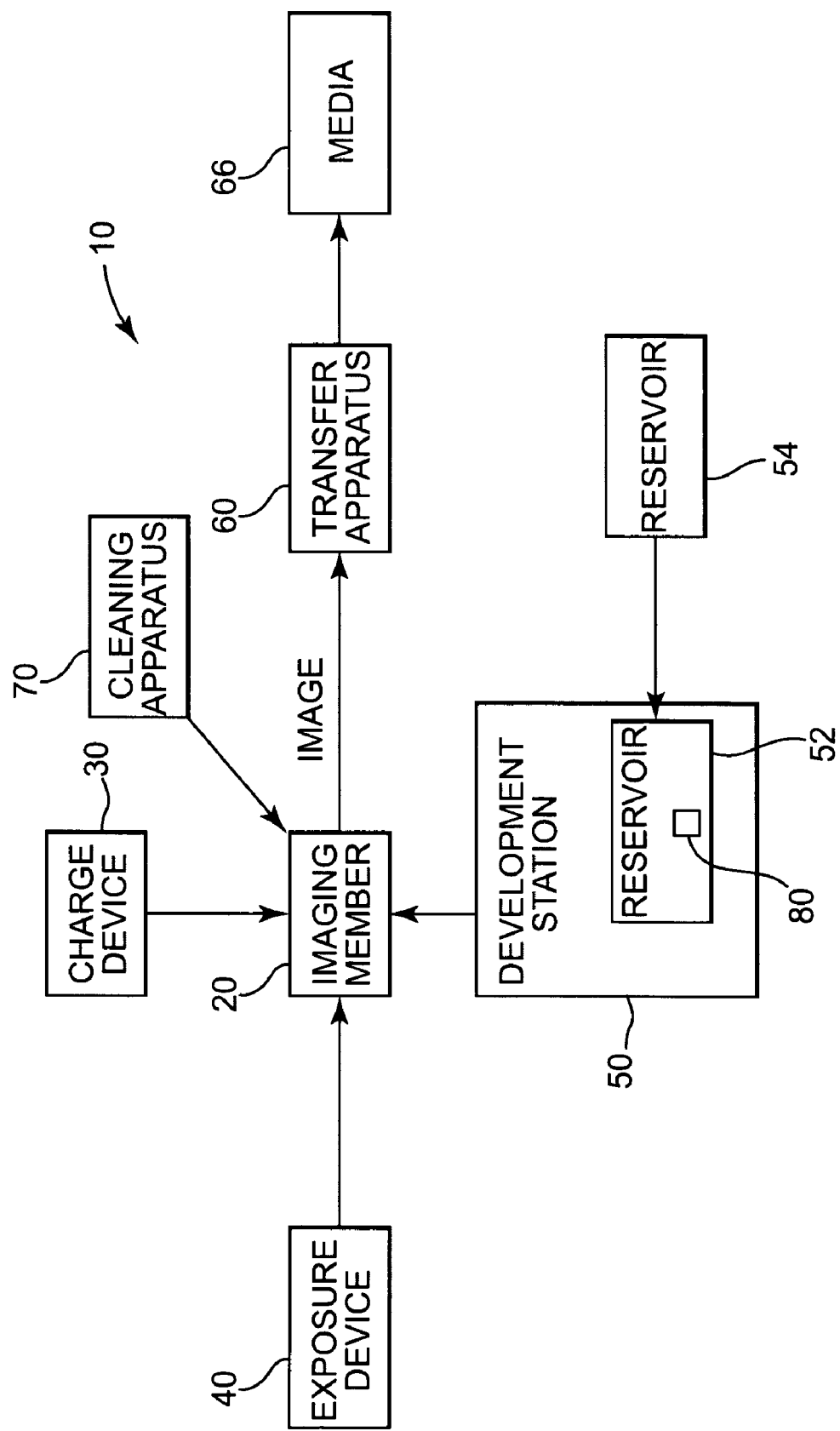
FIG. 1 is a functional block diagram of an image transfer device implementing the apparatus and method for monitoring marking liquid according to one embodiment.
Figure 2:
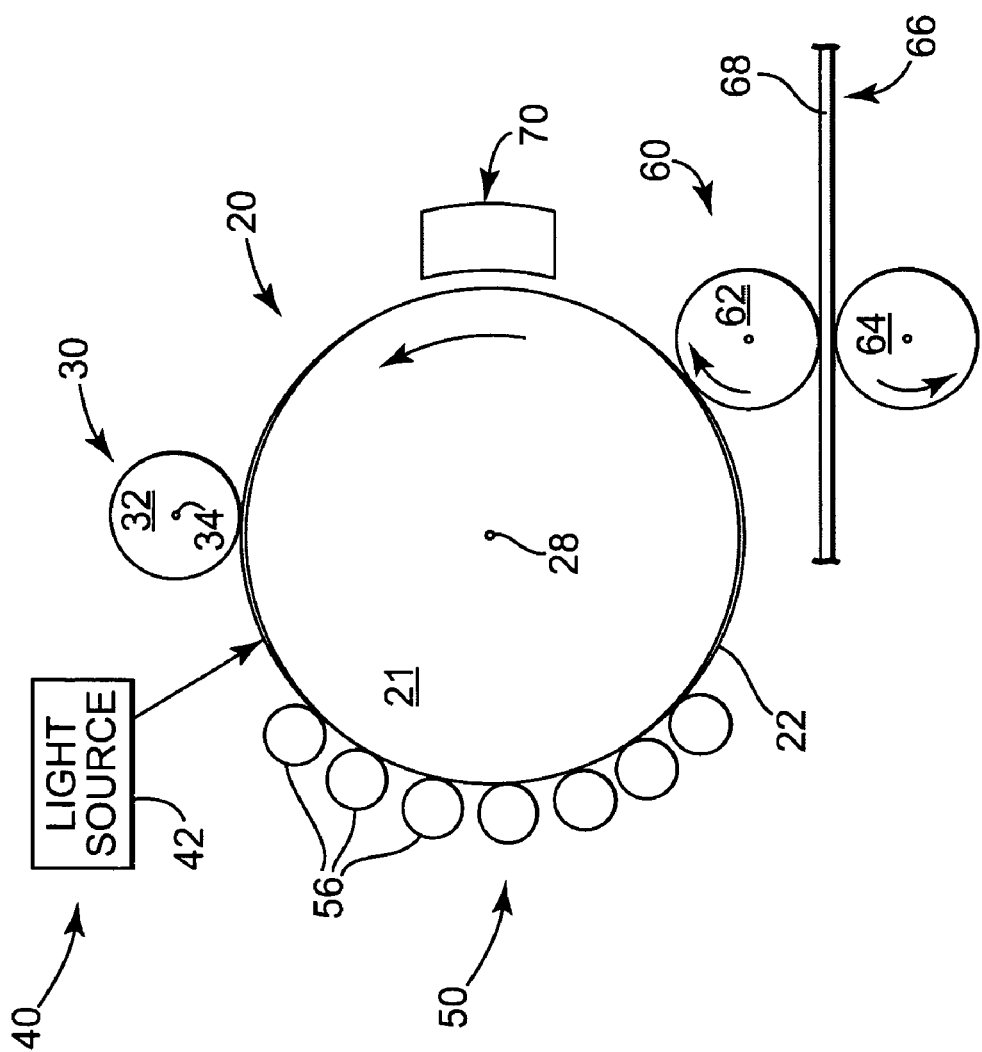
FIG. 2 is a schematic representation of an image transfer device according to one embodiment.

Referring to FIGS. 1 and 2, an exemplary configuration of an image transfer device 10 configured to implement electrophotographic imaging operations according to one embodiment is shown. The depicted image transfer device 10 includes an imaging member 20, a charge device 30, an exposure device 40, a development station 50, an image transfer apparatus 60, and a cleaning apparatus 70. Other configurations are possible, including more, less, or alternative components. Although, for purpose of clarity, embodiments according to the invention are illustrated and described herein with respect to a liquid electrophotographic (LEP) printer having a photoreceptor surface, the invention is understood to be applicable and useful with other embodiments of image transfer devices 10.

Imaging member 20 may comprise a drum 21 (FIG. 2) having photoreceptive surface 22. Images may be formed and developed on photoreceptive surface 22 as further described below. Imaging member 20 may rotate about an axis 28, wherein photoreceptive surface 22 passes adjacent to charge device 30, exposure device 40, development station 50, image transfer apparatus 60, and cleaning apparatus 70. Other configurations of imaging member 20 (e.g., a photoreceptor belt) are possible in other embodiments.

Charge device 30 is configured to provide an electrical charge (typically −500 to −1000 V or 500 to 1000 V) to photoreceptive surface 22 of imaging member 20. Charge device 30 is embodied as a charge roller 32 in the exemplary embodiment shown in FIG. 2. In one embodiment, charge roller 32 is configured to rotate about axis 34 and contact photoreceptive surface 22 of imaging member 20 to provide the electrical charge to photoreceptive surface 22. When charging of the photoreceptor begins, surface 22 is at an electric charge lower than the desired charge. As charge roller 32 moves into close proximity with surface 22, the photoreceptive surface 22 becomes charged. In other embodiments, charge device 30 may be, for example, a corotron, a dicorotron, a scorotron, a discorotron, a pin scorotron, or any other type of charge device as is known in the art.

Exposure device 40 is configured to discharge the electrical charge on photoreceptive surface 22 at selected locations corresponding to a desired image to be formed. The discharging of the electrical charge provides a latent image upon photoreceptive surface 22. In one embodiment, exposure device 40 may be implemented as a light source 42 (such as a laser) that forms an electrostatic latent image on photoreceptive surface 22 by scanning a light beam according to the image to be formed. The electrostatic latent image is due to a difference in the surface potential between the exposed and unexposed portion of photoreceptive surface 22. Exposure device 40 exposes images on photoreceptive surface 22 corresponding to various colors, for example, yellow (Y), magenta (M), cyan (C) and black (K), respectively.

Development station 50 is configured to provide a marking agent to exposed photoreceptive surface 22. The marking agent may be electrically charged and attracted to the discharged locations of photoreceptive surface 22 corresponding to the latent image to thereby develop the latent image. In one embodiment, development station 50 provides a marking liquid, including a mixture of solid particles (i.e., electrostatic toners or electrostatic pigments) dispersed in a carrier liquid (such as isoparaffinic hydrocarbon oil, available under the trade designation Isopar from Exxon Corporation, sometimes referred to as "imaging oil"), to photoreceptive surface 22 of imaging member 20 to adhere the toners or pigments to the portion of photoreceptive surface 22 where the electrostatic latent image is formed, thereby forming a visible toner image on photoreceptive surface 22. The carrier liquid is typically electrically insulative.

Development station 50 is supplied with marking liquid from a reservoir 52 containing marking liquid. In FIG. 1, reservoir 52 is illustrated as located internal to development station 50, but may alternately be located remotely from development station 50. In one embodiment, reservoir 52 is internal to development station 50 and of relatively small capacity and is periodically or continuously resupplied with marking liquid from an external reservoir 54 of relatively large capacity. Referring to FIG. 2, in one embodiment, development station 50 may include a plurality of development rollers 56 which may provide marking liquids having toners or pigments of different colors corresponding to the color images exposed by exposure device 40. Each of the plurality of development rollers 56 may be supplied with marking liquid of an appropriate color from an associated reservoirs 52, 54.

Image transfer apparatus 60 is configured to transfer the toners or pigments of the developed image formed upon imaging member 20 to media 66. In one embodiment, image transfer apparatus 60 includes an intermediate transfer drum 62 in contact with photoreceptive surface 22 of imaging member 20, and a fixation or impression drum 64 defining a nip with transfer drum 62. As transfer drum 62 is brought into contact with photoreceptive surface 22, the toners or pigments of the developed image are transferred from surface 22 to transfer drum 62. Media 66, such as a sheet of paper, is fed into the nip between transfer drum 62 and impression drum 64 to transfer the toners or pigments defining the image from transfer drum 62 to media 66, which may be for example a sheet of paper 68. Impression drum 64 fuses the toner or pigment particles forming the image to media 66.

Cleaning apparatus 70 is configured to remove any toners or pigments which were not transferred from photoreceptive surface 22 to transfer drum 62 prior to recharging of photoreceptive surface 22 by charge device 30. In one embodiment, cleaning apparatus 70 may apply cleaning fluid to photoreceptive surface 22 to assist with the removal of residual toners or pigments. In one embodiment according to the invention, the cleaning fluid is carrier liquid as used in the marking liquid provided by development station 50.

As image transfer device 10 operates and creates images as described above, the carrier liquid and solid particles (i.e., toners and pigments) comprising the marking liquid in reservoirs 52, 54 are gradually consumed. However, different amounts of carrier liquid and solid particles are consumed depending on the content of the pages which are printed. Comparing a printed page having low coverage (in terms of the portion of the page which is covered by the image area) to a printed page having high coverage, the low coverage page consumes more carrier liquid and less solid particles than the high coverage page. Accordingly, carrier liquid or solid particles must periodically or continuously be added to reservoirs 52, 54 as needed to maintain the desired concentration of solid particles in the carrier liquid. In addition, as image transfer device 10 is operated, the temperature of the marking liquid may fluctuate and cause variations in the viscosity and other properties of the marking liquid. Temperature fluctuations of the marking liquid may depend upon factors such as the volume of marking liquid in reservoirs 52, 54, the volume of carrier liquid and solid particles added to the marking liquid in reservoirs 52, 54, the temperature of carrier liquid and solid particles added to the marking liquid, and the amount of heat transferred to the marking liquid by image transfer device 10. Accordingly, there is a need to accurately determine at least one of the concentration of solid particles in the marking liquid and the temperature of the marking liquid.

To determine at least one of the concentration of solid particles in the marking liquid and the temperature of the marking liquid, and thus whether carrier liquid or solid particles should be added to reservoirs 52, 54, a sensor 80 is provided for monitoring the marking liquid. Sensor 80 is illustrated in FIG. 1 as located within reservoir 52. However, in other embodiments, sensor 80 may be located in reservoir 54 or in any portion of the delivery path of the marking liquid to imaging member 20. In one embodiment, a sensor 80 is provided for each color of marking liquid. In one embodiment, more than one sensor 80 may be utilized for each color of marking liquid (e.g., a sensor 80 in each of reservoirs 52, 54). In one embodiment, sensor 80 is not a permanent component of image transfer device 10, and may be selectively installed or coupled with image transfer device 10 to monitor the making liquid. In one implementation, sensor 80 is implemented in a service tool useable with a plurality of image transfer devices.

Figure 3:
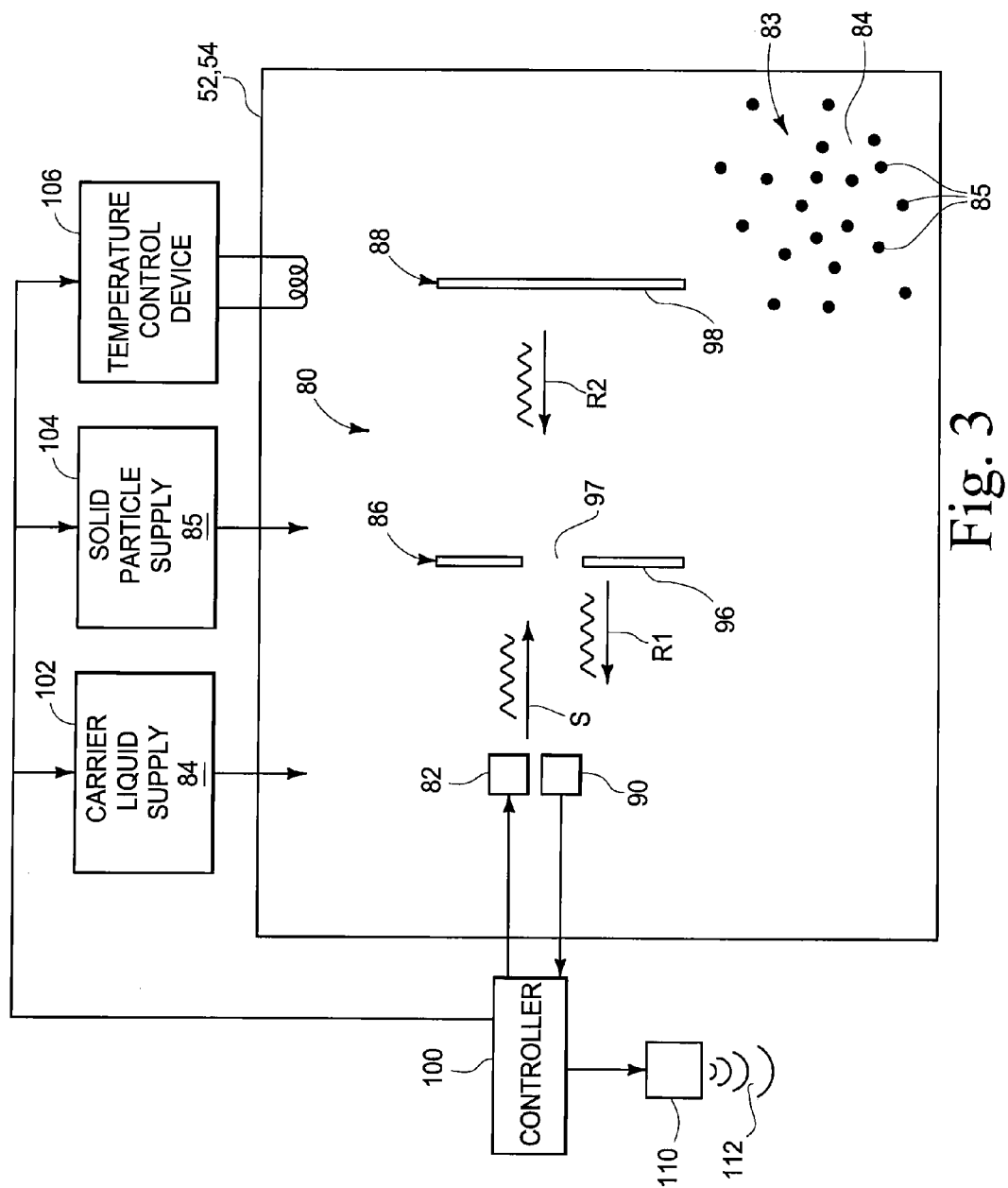
FIG. 3. is a schematic representation of an apparatus for monitoring marking liquid according to one embodiment.
Figure 4:
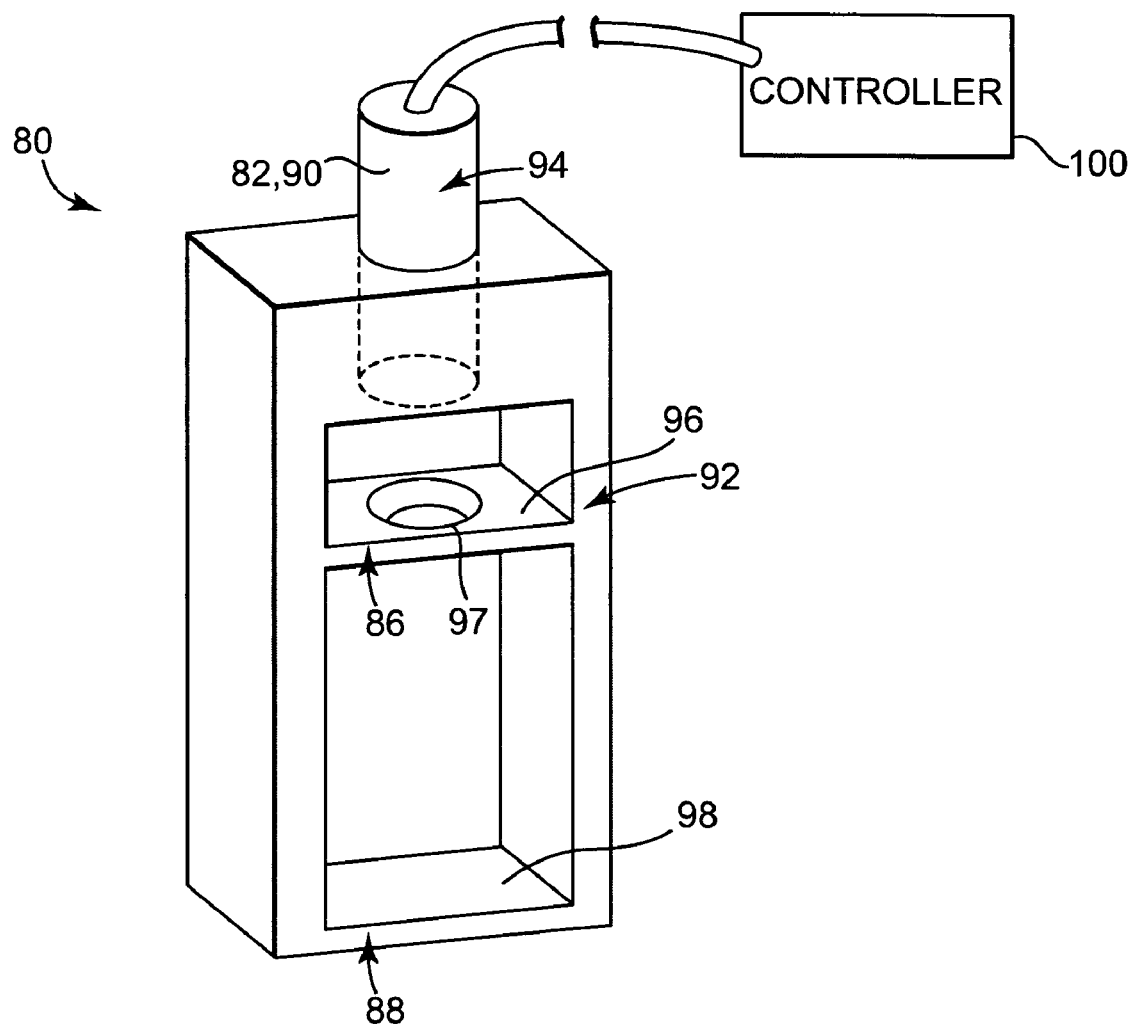
FIG. 4 is a perspective illustration of an apparatus for monitoring marking liquid according to one embodiment.

Referring now to FIGS. 3 and 4, one implementation of sensor 80 according to the invention is illustrated. Sensor 80 includes a transmitter 82 for sending an ultrasonic beam or signal S into marking liquid 83 contained in, for example, reservoir 52 or reservoir 54. Marking liquid 83 includes carrier liquid 84 having solid particles 85 therein. Transmitter 82 is configured to direct ultrasonic signal S toward a first reflector 86 and a second reflector 88. First reflector 86 is configured to reflect a first portion R1 of ultrasonic signal S, and second reflector 88 is configured to reflect a second portion R2 of ultrasonic signal S. A receiver 90 is configured for receiving first and second reflected ultrasonic signals R1, R2, from first and second reflectors 86, 88, respectively. Transmitter 82, first reflector 86, second reflector 88, and receiver 90 are in known positions relative to each other.

Referring to FIG. 4, in one exemplary embodiment, transmitter 82, first reflector 86, second reflector 88, and receiver 90 are configured as a single mechanical assembly 92 to maintain a known and constant geometrical relationship between the components. In the exemplary embodiment of FIG. 4, transmitter 82 and receiver 90 are embodied as a single ultrasonic transceiver 94 that time multiplexes a single ultrasound transducer element. In transmit mode, controller 100 drives the transducer element with a transmit waveform (for example, a sine wave burst). Controller 100 then switches to receive mode, amplifying and digitizing the voltage output from the transducer element when ultrasound energy returns to it and excites it. In one implementation, in transmit mode the transducer element is driven at about 20 volts peak-to-peak in amplitude, and in receive mode the voltage output is in the range of 1 to 100 millivolts peak-to-peak.

First reflector 86 is a partial reflector comprising a planar reflecting surface 96 having an opening 97 extending therethrough. Opening 97 allows a portion of the ultrasonic signal S incident on first reflector 86 to pass through to a planar reflecting surface 98 of second reflector 88. In one embodiment, planar reflecting surfaces 96, 98 have surface variations less than about 1/10 of the wavelength of ultrasonic signal S to reduce wavefront aberration and interference. In one embodiment, ultrasonic signal S has a frequency of 3.5 MHz, with a corresponding wavelength of about 350 microns, and planar reflecting surfaces 96, 98 have surface variations of about 35 microns or less.

A controller 100 is responsive to first and second reflected ultrasonic signals R1, R2 to determine at least one of the temperature of marking liquid 83 and the concentration of solid particles 85 in marking liquid 83. In one implementation, controller 100 is configured to determine an ultrasonic attenuation and ultrasonic velocity of marking liquid 83 using first and second reflected ultrasonic signals R1, R2. Controller 100 then compares the determined ultrasonic attenuation and ultrasonic velocity of marking liquid 83 with known relationships between ultrasonic attenuation, ultrasonic velocity, marking liquid temperature and solid particles concentration to determine at least one of the temperature of marking liquid 83 and the concentration of solid particles 85 in marking liquid 83.

Figures 5A, 5B:
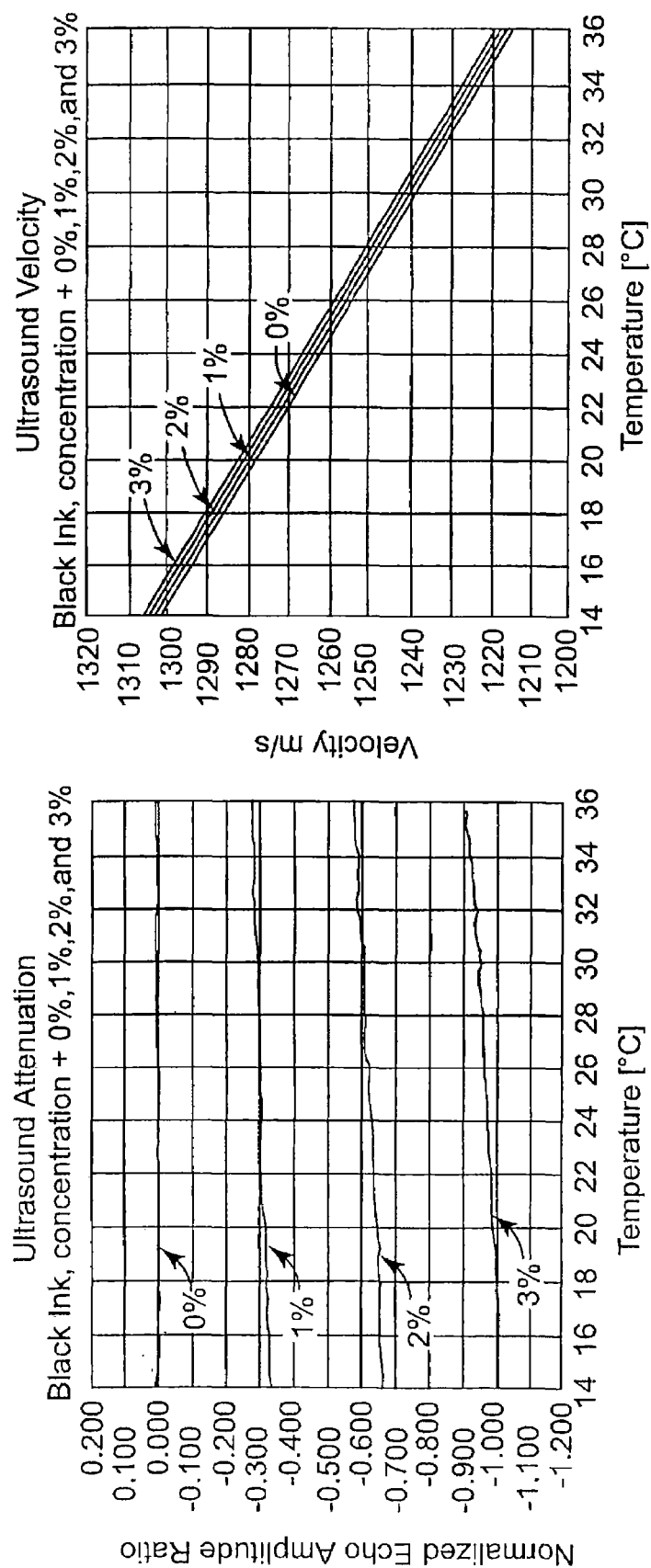
FIGS. 5A and 5B are graphs illustrating relationships between ultrasonic attenuation, ultrasonic velocity, marking liquid temperature and solid particles concentration.

Experimentally determined relationships between ultrasonic attenuation, ultrasonic velocity, marking liquid temperature and solid particle concentration for a range of concentrations of black ink particles are illustrated in the graphs of FIGS. 5A and 5B. Similar relationships may be determined for other colors and concentrations of solid particles. As can be seen from the graphs, ultrasonic attenuation varies strongly with the concentration of solid particles and weakly with temperature (FIG. 5A), while ultrasonic velocity varies strongly with temperature and weakly with the concentration of solid particles (FIG. 5B). Put another way, ultrasound attenuation is closely related to solid particles concentration and not closely related to temperature, while ultrasound velocity is closely related to temperature and not closely related to solid particles concentration. Sensor 80 may be calibrated by making ultrasonic attenuation and velocity measurements on marking fluid samples having known temperature and solids concentration, as shown in FIGS. 5A and 5B. During operation of sensor 80, a best fit of the measured ultrasonic attenuation and velocity data to the calibration data is computed, yielding measured marking liquid temperature and solid particle concentration.

Ultrasonic attenuation has been experimentally demonstrated to be insensitive to the size of solid particles in the marking liquid 83 when the ultrasonic wavelength is much larger than the size of the solid particles 85 (e.g., at least about ten times larger than the size of the solid particles 85). In one experiment, a 3.5 MHz ultrasound frequency (having a corresponding wavelength of about 350 microns) was found to be insensitive to particle sizes of less than about 5 microns. Such results are surprising, as it is commonly understood that the ultrasound wavelength must be comparable to or smaller than the particle size to observe a relationship between ultrasound attenuation and solid particle concentration, as attenuation would normally be the result of scattering or diffraction of the ultrasound waves by the particles. It is also surprising that the ultrasound attenuation is not strongly temperature dependent, because the viscosity certainly is strongly temperature dependent. Without proscribing any particular theory, it is speculated that the ultrasonic attenuation is caused by ultrasonic absorption in the solid phase of the toner and pigment particles 85. Ultrasonic attenuation has also been shown to be insensitive to dissolved polymer resins in the marking liquid, and in addition is insensitive to ink additives such as imaging agents (e.g., charge directors) and release agents (e.g., other oils).

In one embodiment, ultrasonic signal S emitted by transmitter 82 has a frequency near the resonant frequency of transmitter 82. In one embodiment, ultrasonic signal S has a frequency in the range of 100 kHz to 10 MHz. In one embodiment, the ultrasonic signal S has a single frequency. In another embodiment, the ultrasonic signal S may sweep a narrow range of frequencies, such as a range of frequencies surrounding the expected resonance frequency of transmitter 82, so that production variations in the resonant frequency of transmitter 82 may be accommodated (e.g., sweeping from 3.4 MHz to 3.6 MHz for a transmitter expected to have a resonant frequency of 3.5 MHz). The choice of frequency emitted by transmitter 82 is influenced by factors including, for example, the space available for sensor 80 (which limits the size of transmitter 82 and spacing between reflectors 86, 88), the resonant frequency of transmitter 82, dispersion caused by non-uniformities in the volume of marking liquid 83 occupied by the ultrasound beam, and non-uniformities in the reflective surfaces 96, 98 of reflectors 86, 88.

For accurate waveform amplitude attenuation measurements, in one embodiment the ultrasonic signal S may have a duration of about 16 sine wave cycles at the resonant frequency of transmitter 82. At a frequency of 3.5 MHz, 16 cycles results in a signal pulse duration of about 5 microseconds. In other embodiments, ultrasonic signal S may have a duration greater than about 16 sine wave cycles or less than about 16 sine wave cycles. In one embodiment, the length of the emitted ultrasonic waveform is short enough such that the tail end of the emitted waveform does not collide with the leading edge of the waveform reflected from first reflector 86. In one embodiment, to prevent unwanted waveform collisions, first reflector 86 is spaced from transmitter 82 by a distance in the range of 5 mm to 20 mm, and second reflector 88 is spaced from transmitter 82 by a distance in the range of 50 mm to 100 mm.

Referring again to FIG. 3, in one embodiment, a signal device 110 responsive to controller 100 may be provided to produce a signal when at least one of the temperature of marking liquid 83 and the concentration of solid particles 85 in marking liquid 83 are outside of a predetermined range. The signal device 110 may produce an alarm signal 112 indicating the need to add carrier liquid 84 or solid particles 85, or both, to marking liquid 83. In one embodiment, controller 100 automatically controls the addition of carrier liquid 84 or solid particles 85, or both, to marking liquid 83 in reservoirs 52, 54. The addition of carrier liquid 84 or solid particles 85, or both, to marking liquid 83 may continue until the concentration of solid particles 85 is within the desired predetermined range. In one implementation, controller 100 controls a carrier liquid supply 102 containing carrier liquid 84, a solid particle supply 104 containing solid particles 85, and a temperature control device 106 for altering the temperature of marking liquid 83 in reservoirs 52, 54. Temperature control device 106 may be any suitable device for altering the temperature of marking liquid 83, such as a heat exchanger or a resistive heater. Controller 100 compares measured temperature and solid particle concentration values to desired target values, and controls carrier liquid supply 102, solid particle supply 104, and temperature control device 106 to adjust the measured values to the desired target values.

Figure 6B:
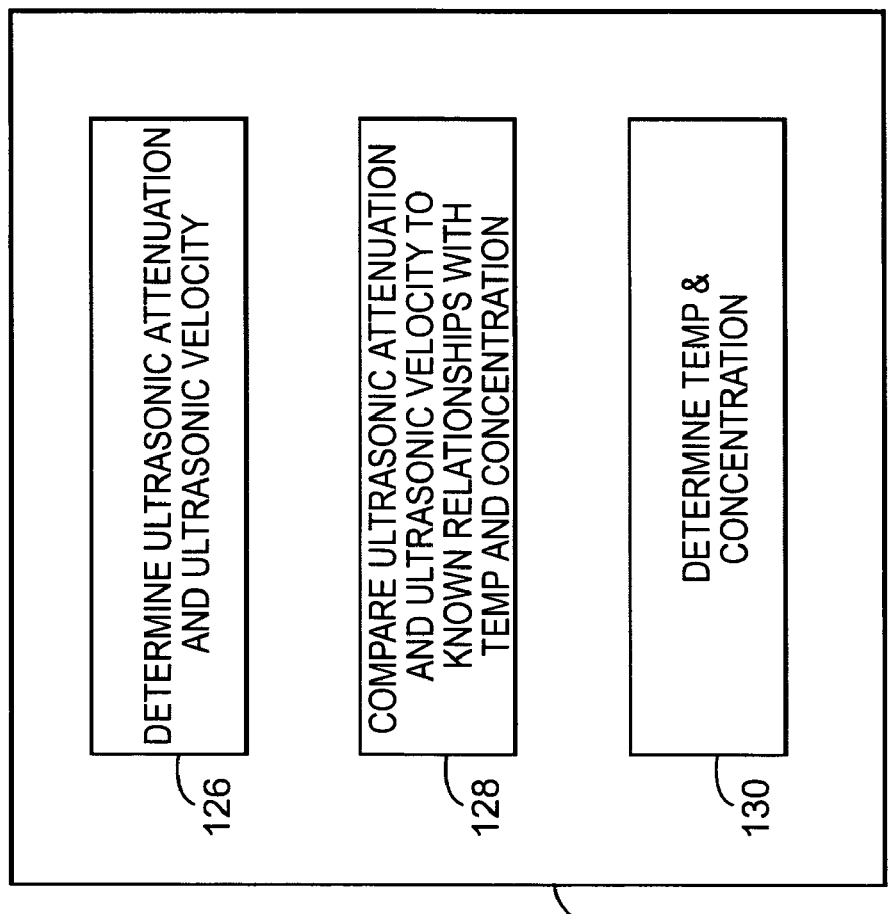
FIGS. 6A and 6B are block diagrams illustrating a method for monitoring marking liquid according to one embodiment.
Figure 6A:
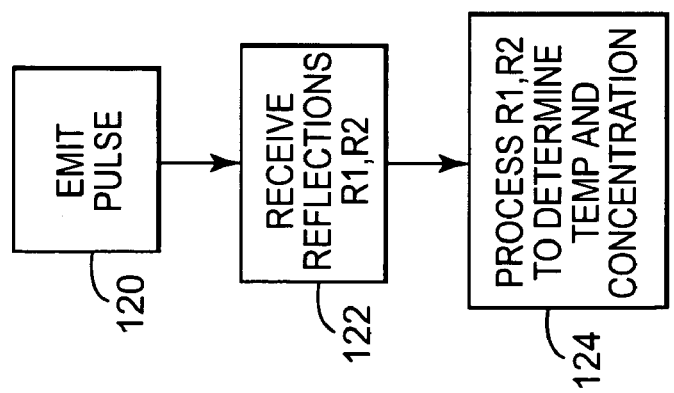

Referring to the flowchart of FIG. 6A, a method of monitoring marking liquid in a reservoir is illustrated. At step 120, an ultrasonic pulse is emitted into the marking liquid 83 toward first and second reflectors 86, 88. At step 122, first reflected ultrasonic signal R1 and second reflected ultrasonic signals R2 are received from first and second reflectors 86, 88, respectively. At step 124, first and second reflected ultrasonic signals R1, R2 are processed to determine at least one of the temperature of the marking liquid 83 and the concentration of solid particles 85 in the marking liquid 83. The received reflected ultrasonic signals R1, R2 may be digitized for digital signal processing.

Referring to FIG. 6B, one implementation of step 124 of FIG. 6A is illustrated. At step 126 an ultrasonic attenuation of the marking liquid 83 and an ultrasonic velocity of the marking liquid 83 are determined. Ultrasonic attenuation of the marking liquid 83 may be determined by qualitatively determining the amplitude of first and second reflected ultrasonic signals R1, R2, and calculating a ratio of the amplitudes of the reflected ultrasonic signals R1, R2, and normalizing the amplitude ratio using a calibration factor determined from the carrier liquid 84 without solid particles 85 therein. Ultrasonic velocity of the marking liquid 83 may be determined using the known distances between first reflector 86 and second reflector 88, and the time interval between the first and second reflected ultrasonic signals R1, R2 when received by receiver 90. In one implementation, during calibration of sensor 80, a polynomial curve is fitted to the measured amplitude ratio of carrier liquid 84 (without solid particles 85 therein) over a range of temperatures (for example, 20 to 35 degrees Celsius). In operation, the estimated temperature is plugged into the polynomial curve to calculate what the amplitude ratio would be at that temperature for the carrier liquid 84 alone. The normalized amplitude ratio equals the measured amplitude ratio of the marking liquid 83 (i.e., carrier liquid 84 with solid particles 85 therein) divided by the calculated amplitude ratio for carrier liquid 84 alone.

At step 128 the determined ultrasonic attenuation and determined ultrasonic velocity are compared with known relationships between ultrasonic attenuation, ultrasonic velocity, marking liquid temperature and solid particles concentration to determine at least one of the temperature of the marking liquid 83 and the concentration of solid particles 85 in the marking liquid 83 at step 130.

Although specific embodiments have been illustrated and described herein for purposes of description, it will be appreciated by those of ordinary skill in the art that a wide variety of alternate and/or equivalent implementations may be substituted for the specific embodiments shown and described without departing from the scope of the present invention. Specifically, ultrasound attenuation and ultrasound velocity in a medium may be measured with any configuration capable of transmitting an ultrasound pulse or signal and receiving it after it has propagated through the medium. Different numbers of transducers, different numbers of reflectors (or no reflectors at all), and different orientations of the various components may be used to measure ultrasound attenuation and ultrasound velocity. This application is intended to cover any adaptations or variations of the preferred embodiments discussed herein. Therefore, it is manifestly intended that this invention be limited only by the claims and the equivalents thereof.

What is claimed is:

1. A method of monitoring marking liquid in a reservoir, the marking liquid including a carrier liquid having solid particles therein, the method comprising:

emitting an ultrasonic signal from an emitter into the marking liquid;

receiving first and second reflected ultrasonic signals from a first reflector and a second reflector, respectively, in the marking liquid, wherein the emitter, first reflector and second reflector are in known positions relative to each other; and processing the first and second reflected ultrasonic signals to determine at least one of the temperature of the marking liquid and the concentration of solid particles in the marking liquid.

2. The method of claim 1, wherein processing the first and second reflected ultrasonic signals comprises:
   determining an ultrasonic attenuation of the marking liquid;
   determining an ultrasonic velocity of the marking liquid;
   comparing the determined ultrasonic attenuation and determined ultrasonic velocity with known relationships between ultrasonic attenuation, ultrasonic velocity, marking liquid temperature and solid particles concentration to determine at least one of the temperature of the marking liquid and the concentration of solid particles in the marking liquid.

3. The method of 2, wherein determining an ultrasonic attenuation of the marking liquid comprises:
   calculating a ratio of amplitudes of the first and second reflected ultrasonic signals; and
   normalizing the ratio using a calibration factor determined from the carrier liquid without solid particles therein.

4. The method of 2, wherein determining an ultrasonic velocity of the marking liquid comprising calculating an ultrasonic velocity using a distance between the first and second reflectors and a time interval between the first and second reflected ultrasonic signals.

5. The method of claim 1, wherein emitting an ultrasonic signal from an emitter comprises emitting a signal having a frequency in the range of 100 kHz to 10 MHz.

6. The method of claim 1, wherein emitting an ultrasonic signal from an emitter comprises emitting a signal having a single frequency.

7. The method of claim 1, wherein emitting an ultrasonic signal from an emitter comprises emitting a signal having a wavelength at least about ten times larger than a size of the solid particles.

8. The method of claim 1, wherein emitting an ultrasonic signal from an emitter comprises emitting a signal having a pulse duration of about 5 microseconds.

9. The method of claim 1, further comprising sending a signal to add at least one of carrier liquid and solid particles to the marking liquid in response to the determined marking liquid temperature and concentration of solid particles.

10. An apparatus for monitoring a marking liquid including a liquid carrier having solid particles therein, comprising:
    a transmitter for sending an ultrasonic signal into the marking liquid;
    a first reflector configured to reflect a first portion of the ultrasonic signal;
    a second reflector configured to reflect a second portion of the ultrasonic signal;
    a receiver for receiving first and second reflected ultrasonic signals from the first and second reflectors, respectively; and
    a controller responsive to the first and second reflected ultrasonic signals to determine at least one of the temperature of the marking liquid and the concentration of solid particles in the marking liquid.

11. The apparatus of claim 10, wherein the transmitter and receiver comprise a single ultrasonic transceiver.

12. The apparatus of claim 10, wherein the transmitter, receiver, first reflector and second reflector are in known positions relative to each other.

13. The apparatus of claim 10, wherein the controller is configured to determine an ultrasonic attenuation and ultrasonic velocity of the marking liquid using the first and second reflected signals.

14. The apparatus of claim 13, wherein the controller is configured to compare the ultrasonic attenuation and ultrasonic velocity of the marking liquid with known relationships between ultrasonic attenuation, ultrasonic velocity, marking liquid temperature and solid particles concentration.

15. The apparatus of claim 10, wherein the transmitter is configured sending an ultrasonic signal having a wavelength at least about ten times larger than a size of the solid particles.

16. The apparatus of claim 10, wherein the first reflector is spaced from the transmitter by a distance in the range of 5 mm to 20 mm, and second reflector are spaced from the transmitter by a distance in the range of 50 mm to 100 mm.

17. The apparatus of claim 10, further comprising a signal device responsive to controller to produce an alarm signal when at least one of the temperature of the marking liquid and the concentration of solid particles in the marking liquid are outside of a predetermined range.

18. An image transfer device comprising:
    an imaging member configured for receiving a latent image thereon;
    a development station configured to develop the latent image of the imaging member using a marking liquid;
    a reservoir supplying marking liquid to the development station, the marking liquid including a carrier liquid having solid particles therein;
    a sensor for monitoring the marking liquid supplied to the development station, the sensor including:
        a transmitter to send an ultrasonic signal into the marking liquid;
        first and second reflectors configured to reflect first and second portions of the ultrasonic signal;
        a receiver for receiving the reflected ultrasonic signals; and
        a controller responsive to the reflected ultrasonic signals to determine at least one of the temperature of the marking liquid and the concentration of solid particles in the marking liquid.

19. The image transfer device of claim 18, wherein the sensor is positioned within the reservoir.

20. The image transfer device of claim 18, wherein the controller is configured to determine an ultrasonic attenuation and ultrasonic velocity of the marking liquid using the first and second reflected signals, compare the determined ultrasonic attenuation and determined ultrasonic velocity of the marking liquid with known relationships between ultrasonic attenuation, ultrasonic velocity, marking liquid temperature and solid particles concentration, and then control at least one of a carrier liquid supply, a solid particle supply, and a temperature control device to adjust the solid particles concentration and marking liquid temperature to desired target values.

21. The image transfer device of claim 18, further comprising a signal device communicating with the controller and configured to produce an alarm signal when at least one of the temperature of the marking liquid and the concentration of solid particles in the marking liquid are outside of a predetermined range.

* * * * *

UNITED STATES PATENT AND TRADEMARK OFFICE
CERTIFICATE OF CORRECTION

PATENT NO. : 7,570,893 B2 Page 1 of 1
APPLICATION NO. : 11/444565
DATED : August 4, 2009
INVENTOR(S) : William David Holland It is certified that error appears in the above-identified patent and that said Letters Patent is hereby corrected as shown below:

In column 9, line 17, in Claim 3, delete "2," and insert -- claim 2, --, therefor.

In column 9, line 23, in Claim 4, delete "2," and insert -- claim 2, --, therefor.

Signed and Sealed this

Sixth Day of April, 2010

David J. Kappos
*Director of the United States Patent and Trademark Office*